United States Patent [19]

Cocola et al.

[11] 4,388,295

[45] Jun. 14, 1983

[54] METHOD AND COMPOSITION FOR DETERMINING HUMAN CHORIONIC SOMATOTROPIN

[75] Inventors: Francesco Cocola, Siena; Paolo Tarli, Monteriggioni; Paolo Neri, Siena, all of Italy

[73] Assignee: Istituto Sieroterapico e Vaccinogeno Toscano "Sclavo" S.p.A., Siena, Italy

[21] Appl. No.: 155,019

[22] Filed: May 30, 1980

Related U.S. Application Data

[63] Continuation of Ser. No. 902,254, May 2, 1978, abandoned.

[30] Foreign Application Priority Data

May 12, 1977 [IT] Italy ............................. 23473 A/77

[51] Int. Cl.$^3$ .................... G01N 33/54; G01N 33/56; G01N 33/58
[52] U.S. Cl. .......................................... 424/1; 435/7; 436/56; 436/527; 436/530; 436/531
[58] Field of Search ................... 424/1, 12; 23/230 B; 435/7

[56] References Cited

U.S. PATENT DOCUMENTS

| 4,034,073 | 7/1977 | Weetall .................................. 424/1 |
| 4,107,284 | 8/1978 | Sultanian et al. ....................... 424/1 |
| 4,120,945 | 10/1978 | Gutcho et al. ......................... 424/1 |
| 4,235,960 | 11/1980 | Basse et al. ............................ 435/7 |
| 4,256,725 | 3/1981 | Rutner et al. .......................... 424/1 |

Primary Examiner—Christine M. Nucker
Attorney, Agent, or Firm—George P. Hoare, Jr.

[57] ABSTRACT

A method and an implementation are disclosed for measuring the contents of a certain component (e.g. a hormone) in a biological fluid. The basic principle of the method is that a complex is formed starting from the antagonist of the component sought for with the product of conjugation of the latter with a tracer (e.g. a radioisotope), said complex is introduced in the biological fluid to be tested and the quantity of the tracer which has been set free is measured with a measuring or dosing technique which is appropriate for the tracer which has been selected.

8 Claims, 4 Drawing Figures

METHOD AND COMPOSITION FOR DETERMINING HUMAN CHRIONIC SOMATROPIN

This is a continuation of application Ser. No. 902,254 filed May 2, 1978 now abandoned.

This invention relates to a method for the determination of the contents of components of biological fluids, said method using a particular complex of the antagonist of the component in which one is interested, with the conjugation product of such component with a tracer compound. In addition, the invention relates to the means which are necessary for carrying out the method in question.

The radio-immunological procedure as used in the clinical practice for determining the contents of antigens or antibodies is known long since and is based on specific reactions in which the former or the latter are involved and on a final separation of the complex from the reaction mixture.

Delving now into details of the method, its basic principle can be summarized as follows:

The reactions which are involved are:

$$L + S \rightarrow L\text{-}S \tag{a}$$

$$L + S^* \leftarrow L\text{-}S^* \tag{b}$$

wherein S is the substance to be dosed, for example, an antigen, and L is the ligand substance (the specific antibody), S* is the substance in question labeled with a tracer (in the radio immunologic technique this is a radioisotrope).

The two reactions reported above, in the practical performance of an analysis, take place simultaneously:

$$2L = S + S^* \rightleftharpoons LS + LS^* \tag{c}$$

Where there is defect of ligand ($L >> S + S^*$), which is then the case which most frequently occurs in practice during progress of an analysis, there is a competition between S and S* to become complexed with L and this possible case can be patterned as follows:

$$2L + 2S + 2S^* \rightleftharpoons LS + LS^* + S + S^*$$

In order to determine the portion of S* which has been bound to L after the competition with S, it is required that the fraction of unreacted S and S* be separated from the respective reaction product (LS and LS*): the measure of the tracer bound to L permits to infer the quantity of S which was present initially in the sample being tested whenever it is possible to have reference to a calibration curve obtained with progressive quantities of standard S.

The competition between the substance in the sample and the substance labeled with the tracer can take place towards a specific ligand such as antibodies, specific binding protein, substrates or inhibitors for enzymes and others, either in a homogeneous or a heterogeneous phase, one of the components can be in the solid phase.

All the conventional methods have the shortcoming that it is necessary to separate the complex from the unreacted substances and, moreover, the reaction times are generally long.

These defects have partially been overcome by using solid supporting members on which the ligands are bound in a number of ways, By so doing, the separation of the complex between the ligand and the substance to be dosed (for example antigen-antibody) from the reaction medium can take place by centrifuging or settling rather than by filtration (with or without washing) as in the conventional methods.

However, in spite of the fact that the methods in solid phase afford advantages over the conventional procedures, the former methods still require a number of steps, such as the accurate measurement of the sample to be analyzed, the distribution of the radioactive material (in liquid form) and, in a few cases, the distribution of the solid phase, such steps being potential sources of errors.

In addition to the foregoing, the necessity of labeling a certain quantity of the substance to be dosed directly before the analysis, and the use of the substance as such involves other disturbances the first of which is the obligation to purify the substance concerned from possible degradation products and from the excess of tracer; such a purification step influences, consistently with its intensity, the results of the analysis somewhat.

We have now found, and this is a first characteristic feature of the present invention, that all the drawbacks enumerated above can be offset by the provision of a method for the determination of components of biological fluids wherein use is made, to that purpose, of a complex which is composed by the antagonist of the component concerned and by the product of conjugation of the latter with a tracer.

More particularly, the subject matter of this invention is an improved method for the determination of the quantity of components of biological fluids, said method comprising the following basic operation:

forming a complex starting from the antagonist of the component concerned and from the product of conjugation of the latter with a tracer;

introducing said complex in the solution which contains the component to be dosed;

measuring the quantity of tracer which has been set free; again, the contents in the sample being tested is determined by having reference to a calibration curve as obtained with progressive quantities of the substance to be dosed at known concentrations.

The method in question can be carried out, both directly in the liquid phase, and by employing solid supporting members. In the one case as in the other, the defects inherent in the prior art methods are completely set aside, both in the case that a solid support is adopted and in the case that no such support is used. For example, in the case of the adoption of radioisotopes, the radioactivity to be used is reduced to very low levels and it is not necessary to manipulate the radioactive substances with pipettes or other sources of possible pollution. The labeled substance, which is introduced in the reaction, is surely immunoreactive, that which involves an improvement of the sensitivity of the method.

When a solid supporting member is used, it is not necessary exactly to measure the volumes of the samples to be tested because the accuracy of our method is entrusted to the accuracy of the reactive surfaces of the supporting members and this is obtained prior to carrying out the analysis.

It is also possible, similarly to what occurs with other methods, to check the analytical operation since the quantity of the tracer can be measured both in the solution and in the starting complex.

It is also possible, and this is another feature of this invention, to prepare kits having a size smaller than that of the present commercial kits, that which is a not negligible advantage.

Such kits are formed by the above defined complex, the latter being, in its turn, a further feature of the present invention, and by a set of reference standards, of known concentration, of the component concerned, such standards enabling the plot the calibration curve.

Apparently, to the ends of the present invention, the complex which is a part of the commercial kit can be present as such or it can properly be affixed to a solid supporting member. The insolubilization of the complex is carried out with the usual procedures as known to those skilled in the art and also the supporting member is selected from among those which are being commonly employed for carrying out the conventional methods. These supporting members are generally selected from among cellulose (a powder or as paper), cellulose with particular reactive groups such as carboxymethyl- or diethylaminoethyl- (still in the forms of powder or paper), plastics materials such as polyvinyl chlorides, polystyrene, nylon, polymetacrylates, polyamides, ureic resins, cellulose acetate, nitrate, triacetate, cellulose esters or ethers and their derivatives, and glass.

The substance to be determined, in its turn, is labeled, prior to forming the complex, by means of tracers according to the conventional procedures, these tracers being of different types according to the sensitivity which is requested. Among the tracers which can be preferably used, the following can be indicated:

radioisotopes such as $I^{125}$, $I^{131}$, $H^3$, $C^{14}$, $Co^{57}$ and others fluoroscent substances, such as fluoroscein isothiocyanate, rhodamine and derivatives, and others dyestuffs, such as eosin, Comassie Blue and others enzymes, such as peroxidase, glucose oxidase, carbonic anhydrase, ferricyanide dependent- or NAD-dependent lactic dehydrogenase and others.

inhibitors of certain reactions, for example of enzymatic reactions and of non-enzymatic reactions (in the case of inhibitors of enzymatic reactions, compounds which contain sulphonamide groups which are potent inhibitors for the carbonic anhydrase enzyme can be used: examples of such compounds are benzenesulphonamide and p-carboxybenzenesulphonic acid), complex-forming substances (for example EDTA) which can cause the concentrations of certain elements to vary in the medium being tested.

The labeled substance which has been obtained in this way is then used to prepare the insoluble complex which has been mentioned in this specification many a time. The preparation of such complex is an integral part of the present invention and can be detailedly indicated as follows:

The insolubilized ligand substance is put to react with a strong excess of the labeled substance (homologous) in order to saturate all the available ligand groups. The reaction is allowed to proceed at 37° C. overnight (20 hours). The solid phase is recovered and washed with water until the excess of the labeled substance has completely been discharged. The solid phase is dried in air and stored at 4° C. is an airtight pouch till the time of use. The limits of variability of the labeled complex depend on the time of labeling used.

What has been disclosed in the foregoing and other details will be further delucidated by the subsequent operative steps: these, however, are not to be construed as limitations of the invention.

In order to check the validity of the invention, a method has been optimized for the dosage of a hormone of placental origin, the Human Chorionic Somatomammotropin (HCS). This hormone circulates in the blood plasma of pregnant women in an increasing concentration the entire pregnancy period throughout (at least in normal cases). To know the HCS level is a considerable aid for monitoring the trend of the foeto-placental union. The method, and its technical advantage for the preparation of the several reagents, is reported hereinafter.

MATERIALS

HCS: The 48/80 lot was prepared in the Assignee Laboratories according to the method by Neri et al., disclosed in "Ann. Sclavo", 12,663 (1970), Labeled hormone: $^{125}$I-HCS was prepared using the enzymatic labeling procedure reported hereinafter.

To 5 micrograms of HCS (in 10 mls of 0.05 M phosphate buffer, pH 7.5) there are added, in the order given:

1 mCi (10 microliters) of carrier free Na-$I^{125}$(Amersham)

1 microgram of lactoperoxidase (calbiochem B grade), 30.5 IU/milligram, 0.1 microgram (10 microliters) of $H_2O_2$ (Peridrol Selectipur, 30%, Merck).

After a 10-minute wait, add a supplement of 10 microliters of $H_2O_2$ and wait 10 additional minutes.

The labeled hormone is deiodized on Zerolit ($1 \times 8$), eluted with a Barbital buffer, 0.05 M, pH 8.6, 9.5% fraction V of bovine seroalbumin (BSA) and finally purified on Sephadex-G-100 in phosphate buffer 0.04 M, pH 7.4, 0.1% BSA. The so labeled $^{125}$I-HCS has a specific activity of 140 microCi/microgram.

$^{125}$I-HCS labeled with chloramine-T was obtained from CIS (Italy) at a specific activity of 60 microCi/microgram.

Antibodies

The anti-HCS serum is obtained from goats by inoculating them 5 Times with 5 milligrams of HCS in complete Freund adjuvant every 15 days and blood-letting 10 days as from the last reactivation injection. The titre, checked with radioimmunologic assay (method of the double antibody) at 50% of maximum bond must not be less than 1/64,000. The gamma-globuline from such serum were prepared by precipitation with $Na_2SO_4$, at 18% (R. A. Kekwich, Biochem., J., 34, 1248 (1940). The proteinic concentration was 60 milligrams per milleliter after purification (final solution).

Preparation of the anti-HCS antibodies bound to the cellulose (discs)

Cellulose discs were clipped off, having a diameter of 5 millimeters from laboratory filter paper (465 discs were equivalent to about 1 gram of cellulose). The discs were activated with BrCN (L. WIDE, Acta Endocrinologica Kbh., 63, (Suppl. 142), 207, (1969)) and covalently coated with anti-HCS gamma-globulins.

The paper discs (10 grams) were placed in a glass vessel containing 200 mls of sodium bicarbonate 0.1 molar, pH 8, containing anti-HCS gamma-globulins.

The suspension was kept at room temperature for 18 hrs. at a pH kept constant at 8 and with stirring. The discs were subsequently treated for 5 hours at room temperature with a solution (1 milligram per ml) of ethylenediamine, pH 9.3 so as to neutralize the active groups which were left free on the cellulose. The cellulose discs were then washed with $3 \times 200$ mls of 0.1 M $NaHCO_3$, with 0.1 M, pH 4 acetate buffer ($3 \times 200$ mls) and with $3 \times 200$ mls of 0.04 M, pH 7.4, 0.1% BSA at room temperature. The discs having covalently bound antibodies were freeze-dried and kept at 4° C. in a sealed tin, till the time of use.

Preparation of the Ab/$^{125}$I-HCS complex

The paper discs coated with anti-HCS gamma globulins are glued to $0.5 \times 7$ cm plastics strips having a thickness of 1 millimeter and then soaked in a solution of $^{125}$I-HCS in 0.04 M, pH 7.4 phosphate buffer at a concentration of 300,000 cpm/ml (1500 mls are enough to prepare 4650 discs) and incubated at 37° C. overnight. The discs are then washed in $H_2O$ (or phosphate buffer), dried 3 hours in air and sealed in airtight pouches made with plastics and aluminum and heat-welded (30 discs per pouch) and maintained at 4° C. till the time of use.

Results.     Basic principle of the method.

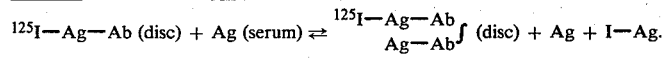

The addition of antigen in solution to a $^{125}$I-Ag-Ab solid complex encourages the substitution, in the complex, of $^{125}$I-Ag by unlabeled Ag. The $^{125}$I-Ag which has passed in solution can be counted out after that the paper disc which contains the residual $^{125}$I-Ag-Ab has been removed from the system. The quantity of $^{125}$I-Ag released in solution will be proportional to the concentration of Ag contained in the sample being tested.

Definition of the optimum reaction conditions

Incubation time and temperature

FIG. 1 displays the release kinetics (c.p.m. against hours of incubation) both in the absence and in the presence of HCS (500 nanograms per ml) in the incubation medium, at four different temperature levels, viz.: 4° C., 20° C., 37° C., 45° C.

As it is shown, the release is increased as the temperature is increased in incubation. The ratio of the quantity which is released with no HCS being present to that which is released when HCS is present remains virtually constant in time and irrespective of the temperature of incubation, whereas the difference becomes ever and ever greater as the temperature is increased. By adopting a higher temperature, a sharper discrimination will be obtained at the lower concentrations of the hormone. Upon taking all these factors into considerations, the temperature which has been selected is 37° C.

The selection of the time of incubation is governed by the sensitivity of the required method on the basis of the results displayed in FIG. 1.

Concentration of the antibody bound to the paper disc

To paper disc are attached, as outlined above, gamma-globuline from anti-HCS goat serum at the following concentrations: 18.0-1.8-0.36 and 0.09 milligrams per gram of paper, respectively. The first concentration corresponds to the undiluted preparation. The discs, after drying, are incubated with $^{125}$I-HCS (300,000 cpm/ml) and the Ab/$^{125}$I-HCS complex is used for obtaining dose-response curves from 5 nanogram/ml to 200 nanogram/ml of HCS. The curves obtained after 18-hour incubation at 37° C. are reported in FIG. 2. As can be seen, there is a definite loss of sensitivity as a function of the decrease of the concentration of the Ab bound to the disc. The concentration which was adopted was thus that of 18 milligrams per gram, also for the results of the sensitivity tests.

Disc surface

By maintaining the quantity of Ab (18 milligrams per gram of paper) constant per surface unit, the total amount of Ab which was present in total was decreased by causing the area of the paper disc to be decreased, viz.: 23.0-11.5- 5.7 and 2.8 square millimeters. The standard curves from 2.5 to 200 nanograms of HCS are plotted in FIG. 3.

As can be seen, as the cross-sectional area is decreased there is a decrease of the sensitivity of the method. The area which was selected for the discs was then 23.0 square millimeters.

Concentration and validity of the labeled hormone

Remarkable differences have been found by using two different kinds of labeled hormone. Those labeled with chloramine-T are less intensively bound to the testing paper with Ab and the Ab/$^{125}$I-HCS complex is more easily displaceable than that obtained with HCS which has been labeled using lactic acid peroxidase.

The concentration of $^{125}$I-HCS used to form the Ab/$^{125}$I-HCS complex, and thus the concentration bound to the paper disc does not modify the ratio between the "bursts" delivered in the presence of the hormone and those delivered with no hormone being present (TABLE 1). The difference between the number of bursts of the samples and the number of bursts of the background undergoes conversely, a considerable decrease as the quantity of bound labeled hormone is decreased (TABLE 1).

Reaction volume

The minimum required volume in order that a disc having an area of 21.0 square millimeters may covered by the serum is 0.3 ml (in test tubes having an inside diameter of 0.8 cm). The same dosages have been effected (equal concentrations of hormone) by immersing the disc (supported by the plastics strip) in the volumes of 0.3-0.6-0.9 and 1.2 ml of the solution being tested. TABLE II reports the bursts delivered in 18 hours of incubation at 37° C. in a solution of serum which did not contain HCS and in solutions containing 5, 20, 100 and 500 nanograms per milliliter of HCS concentration. By doubling the volumes, that is, passing from a volume of 0.3 to 0.6, there are no significant differences in the quantity of released hormone. At higher volumes, the release at the lower values has been increased, whereas, for concentrations over 5 nanograms per ml of HCS there is no appreciable difference between the burst released in 0.3 ml and those released in 1.2 ml.

Specificity

In order to assess if in the suggested system the cross reaction exhibited by HGH (Human Growth Hormone, a somatotropic hormone) was identical to that experienced with a normal radioimmunologic dosage by competition, increased quantities of HGH have been added to a human serum deprived of HCS and placed to incubate at 37° C. for 18 hrs. with the Ab/$^{125}$I-HCS complex. Until 50 nanograms are added no shift significantly different from that of the background is seen. The highest assayed dose of HGH (1,000 nanograms) gives an Ro/Rc of 0.72, which is equivalent to the average shift caused by 25 nanograms per ml of HCS.

Stability tests

Stability of the Ab test paper strips

The paper strips dried by freeze-drying and sealed in an airtight container remain virtually stable if kept at 4° C. As a matter of fact, tests carried out at 2-3 month intervals as from the preparation give the same results, that is, are capable of fixing always the same quantity of labeled hormone.

Stability of the Ab/$^{125}$I-HCS on the test paper strips

In order to extend the duration of the time of use of the $^{125}$I-HCS/Ab solid complex, a number of stabilizing treatments have been tried: serum, glycerol (15%), formaldehyde, drying over CaCl$_2$, P$_2$O$_5$, drying with acetone and air drying. Nearly all of these treatments impair the Ab/$^{125}$I-HCS complex, with the exclusion of the mere drying at room temperature in air. Drying after incubation in a serum containing no HCS lowered the backgrounds (decrease of the radioactivity level released in a serum containing no HCS). The paper strips with the complex, dried and sealed in airtight pouches, can be used for at least 32 days if they are stored at 4° C. At any rate, the aging of the labeled hormone is conducive to a flattening of the standard curve with a constant lift of the radio activity fraction set free at the zero concentration of antigen, the result being an impairment of the sensitivity. In order that such a drawback may be offset it is sufficient, however, to wash the paper test strips with the complex Ab/$^{125}$I-HCS beforehand with serum containing no HCS, at 45° C. for 45 minutes. In our tests, we have used this washing procedure starting from the 15th day as from the preparation.

Optimization of the HCS-dosing methods

From that which has been reported hereinbefore, it is possible to derive two kinds of dosage for HCS: the one is a high-sensitivity method which can be used in the range from 1 to 200 nanograms/ml with a time of incubation of 18 hrs at 37° C., called method A, and another method, optimized for the dosage of HCS during pregnancy (100–700 nanograms/ml) with an incubation time of 3 hrs at 37° C., and this is the method B. TABLE III describes the two optimized methods. The standard curves which have been obtained are reported in FIG. 4, which also reports the trend in the two methods of the standard curves after 32 days of storage of the paper strips at 4° C. TABLE IV, lastly, reports the analytical parameters of the more sensitive method suggested hereby (method A).

Discussion

In order to assess which was the maximum sensitivity of the method suggested for HCS, the following parameters have been caused to vary: temperature, incubation time, concentration of the Ab/$^{125}$I-HCS complex. The temperature acts by encouraging the substitution of $^{125}$I-HCS by cold HCS, possibly due to the increased number of collisions which can occur. Also the spontaneous release is increased but what is of the utmost importance is that at longer times of incubation the difference between the specifically released bursts and those released with HCS being present is increased. This fact permits to have a wider field available for plotting the standard curve. The decrease of the concentration of the Ab/$^{125}$I-HCS can be obtained in a number of ways, viz.:

(a) by diminishing the concentration of the insolubilized ligand (Ab)
(b) by reducing the surface area of the paper disc coated with Ab/$^{125}$I-HCS
(c) by decreasing the quantity of $^{125}$I-HCS bound to the Ab paper disc.

The decrease of the concentration of Ab has given a response contrary to that which was expected. As a matter of fact, as the concentration of Ab is decreased, the sensitivity of the method is also decreased, down to a complete flattening of the Ro/Rc curve (FIG. 2).

It is to be borne in mind that the quantity of $^{125}$I-HCS bound to the disc, coated with the lower concentration of antibody is 14,000 cpm as compared with the 43,000 cpm bound to the discs coated with the highest concentration of antibody. Also the addition of 8 micrograms of HCS does not displace from the background the hormone bound thereto in a significantly different way. This fact could be an evidence that the stability of the Ab/$^{125}$I-HCS complex is improved as the quantity of antibody by which the paper is coated, is decreased. Presumably, the use of variable quantities of Ab for sensitization changes the arrangement of the molecules of gamma-globulins on the paper surface and has an influence on the energy of bonding with the corresponding antigen. In order to try and find a confirmation of such a speculation, an attempt has been made towards carrying out the method in the liquid phase (where the antigen, also in this case HCS, has not undergone any change, as it is apparent). The radioactivity of the complex formed at 4° C. has not been charged any more by increasing concentrations of HCS. The reversibility is a function of the form of the complex, a form which is determined, in its turn, by the relative concentrations of antibody and of antigen with which the complex is obtained. The reaction is thus particularly reversible under the conditions studied by ourselves. Even by decreasing the disc area and by keeping the concentration of Ab/$^{125}$I-HCS unaltered, a drop of sensitivity of the standard curve has been observed. This result can be due to the fact that the probability of replacement of $^{125}$I-HCS by HCS becomes smaller and smaller as the number of possible collisions is decreased because of the decrease of the exchange surface. The sensitivity of the reaction does not change when the concentration of Ab is left unaltered and a smaller quantity of labeled hormone is bound. The small sensitivity to the variations of volume indicates that the method depends from the concentration and that the exchange takes place in the interfacial layer between the liquid and the solid phase. For wider variation of volume (3 to 4 times the adopted volume of 0.3 ml) the effect becomes appreciable and, more particularly, at the low concentrations of hormone. On these bases, two methods have been optimized with two different sensitivities. Either method is for dosing the HCS in the clinical diagnostic field and the other is for studying the sensitivity of the system. The standard curves reported herein, even if they differ from the 7th to the 32nd day, give values of plasma dosages which can be compared within the range of the kind of dosage which is adopted. The foregoing is such as to enable us to affirm, eventually, that the method suggested hereby affords advantages over the conventionally known methods. Its characteristic features, such as the drastic reduction of the number of steps, the indipendence from the reaction volume, the sufficient sensitivity, the rather long validity time can contribute towards making such type of analysis (and more particularly the radioimmunological dosages) a routinely laboratory practice.

TABLE I

INFLUENCE OF THE QUANTITY OF LABELED HORMONE BOUND TO THE PAPER TEST STRIP ON THE STANDARD CURVE

| $^{125}$I-HCS cpm/ paper strip | cpm/c0 | cpm/ c5 | cpm/ c250 | $\frac{c5}{c0}$ | $\frac{c250}{c0}$ | Δ cpm c5-c0 | Δ cpm c250-c0 |
|---|---|---|---|---|---|---|---|
| (a) 57815 | 2879 | 4079 | 12578 | 1.40 | 4.30 | 1200 | 9699 |
| (b) 28310 | 1452 | 1843 | 6002 | 1.30 | 4.10 | 395 | 4550 |
| (c) 13785 | 749 | 1108 | 2702 | 1.40 | 3.60 | 359 | 1953 | c0 = number of bursts released after 18 hrs at 37° C. in 0.3 ml of serum containing no HCS
c5 = number of bursts released after 18 hrs at 37° C. in 0.3 ml of serum containing 5 nanograms/ml of HCS
c250 = number of bursts released after 18 hrs at 37° C. in 0.3 ml of serum containing 250 nanograms/ml of HCS
The coefficient of variation, in percentage, of the values tabulated above, calculated on 5 replicas, is in the order of 6% to 8%.

TABLE II

| Sample volume | H C S, nanograms per milliliter | | | | |
|---|---|---|---|---|---|
| mls | 0 | 5 | 20 | 100 | 500 |
| 0.3 | 3758 | 5019 | 7078 | 9594 | 12594 |
|  | ±50 | ±41 | ±566 | ±700 | ±347 |
| 0.6 | 3718 | 5452 | 6979 | 10496 | 11313 |
|  | ±58 | ±365 | ±419 | ±382 | ±749 |
| 0.9 | 5213 | 6474 | 7388 | 10774 | 11690 |
|  | ±150 | ±75 | ±450 | ±261 | ±1500 |
| 1.2 | 5270 | 6047 | 7154 | 10484 | 12082 |
|  | ±232 | ±492 | ±615 | ±512 | ±637 |

Six samples have been tested for each test run and the mean is reported, ± the standard deviation.

TABLE III

METHODS FOR DOSING PLASMATIC HCS
In plastics tubes (0.8 × 10 mm) add, in the order given:

| A | B |
|---|---|
| 0.3 ml of serum to be tested or of standard serum (from 1 to 200 nanograms/ml of HCS) | 0.3 ml of serum to be tested or standard serum (100 nanograms/ml-7000 nanograms/ml of HCS) |
| Paper strip Ab/$^{125}$I-HCS* 18 hrs at 37° C. | Paper strip Ab/$^{125}$I-HCS 3 hrs at 37° C. |
| Remove paper strip | Remove paper strip |
| Count medium | Count medium |

*The Ab/$^{125}$I-HCS paper strip must be washed before use for 45 mins at 45° C. in 0.3 ml of serum without HCS.

TABLE IV

| ANALYTICAL PARAMETERS (METHOD A) | |
|---|---|
| Sensitivity | 1.5 nanograms/ml at 95% of Ro/Rc |

TABLE IV-continued

| ANALYTICAL PARAMETERS (METHOD A) | |
|---|---|
| Specificity | 2.5% crossed reaction with HGH |
| Precision | |
| Between assays* | coeff. of variation 17% |
| Within assays** | coefficient of variation 12% |
| Accuracy*** | 0.96 |
| Validity of the reagent at least 32 days | |

*Expressed as mean coeff. of variation for three dosage levels (low, average, high) of HCS with 10 replicas, for each point.
**Expressed as average coeff. of variation calculated at three dosage levels (low, average, high) on 11 subsequent dosages during the 32 days of validity of the reagents.
***Calculated with respect of the values of HCS in the serum as determined with the method of the double antibody taken as a reference.

Release of the labeled HCS in the incubation medium with reference to time, at different temperatures of incubation, with and without the addition of 500 nanograms per ml of HCS: the abscissae are the times in hours and the ordinates are cpm. $10^{-3}$ in the medium.

| 4° C. | 4° C. with 500ng/ml HCS |
| Δ 20° C. | Δ 20° C. with 500ng/ml HCS |
| □ 37° C. | □ 37° C. with 500ng/ml HCS |
| * 45° C. | + 45° C. with 500ng/ml HCS |

FIG. 2

Standard curves obtained with paper discs which have been sensitized and various concentrations of Ab. Ro shows the cpm released with no HCS being present and Rc the cpm released when the medium contains the HCS concentrations reported on the abscissae. The abscissae are the concentrations of HCS in nanograms/ml. The ordinates are the ratio of Ro to Rc.

+ 0.09 milligrams of G/g of cellulose
0.36 milligrams of G/g of cellulose
Δ 1.80 milligrams of G/g of cellulose
□ 18 milligrams of G/g of cellulose

FIG. 3

Figure 1:
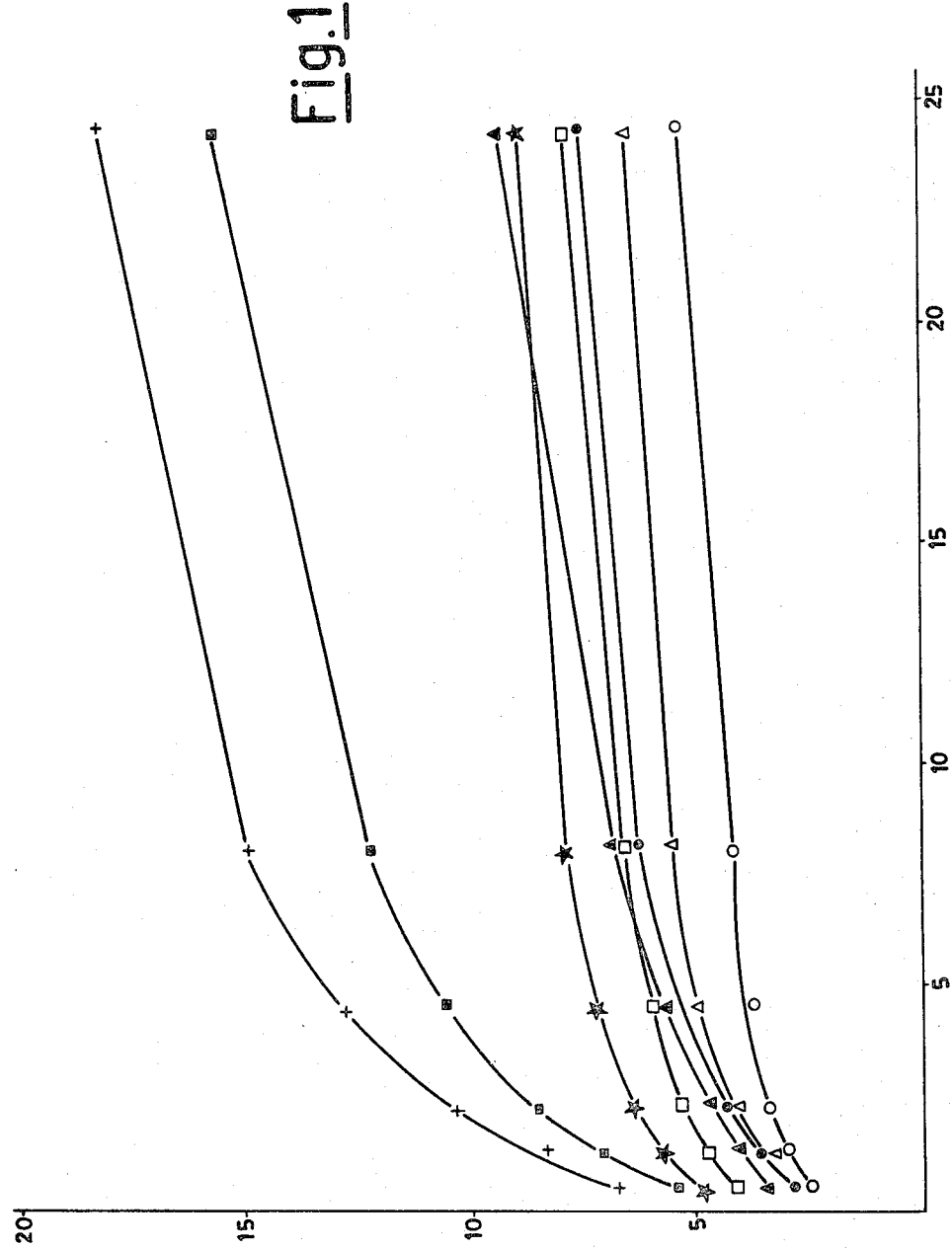
FIG. 1
Figure 2:
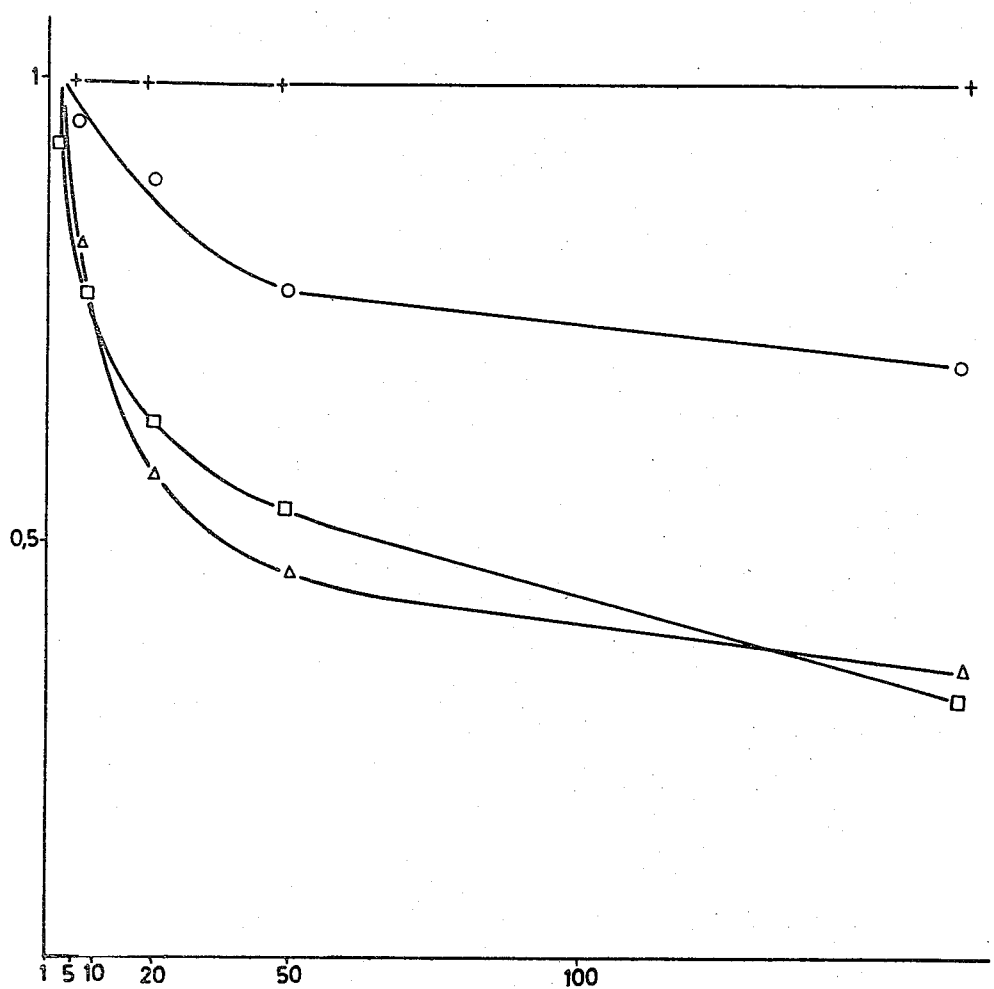
Figure 3:
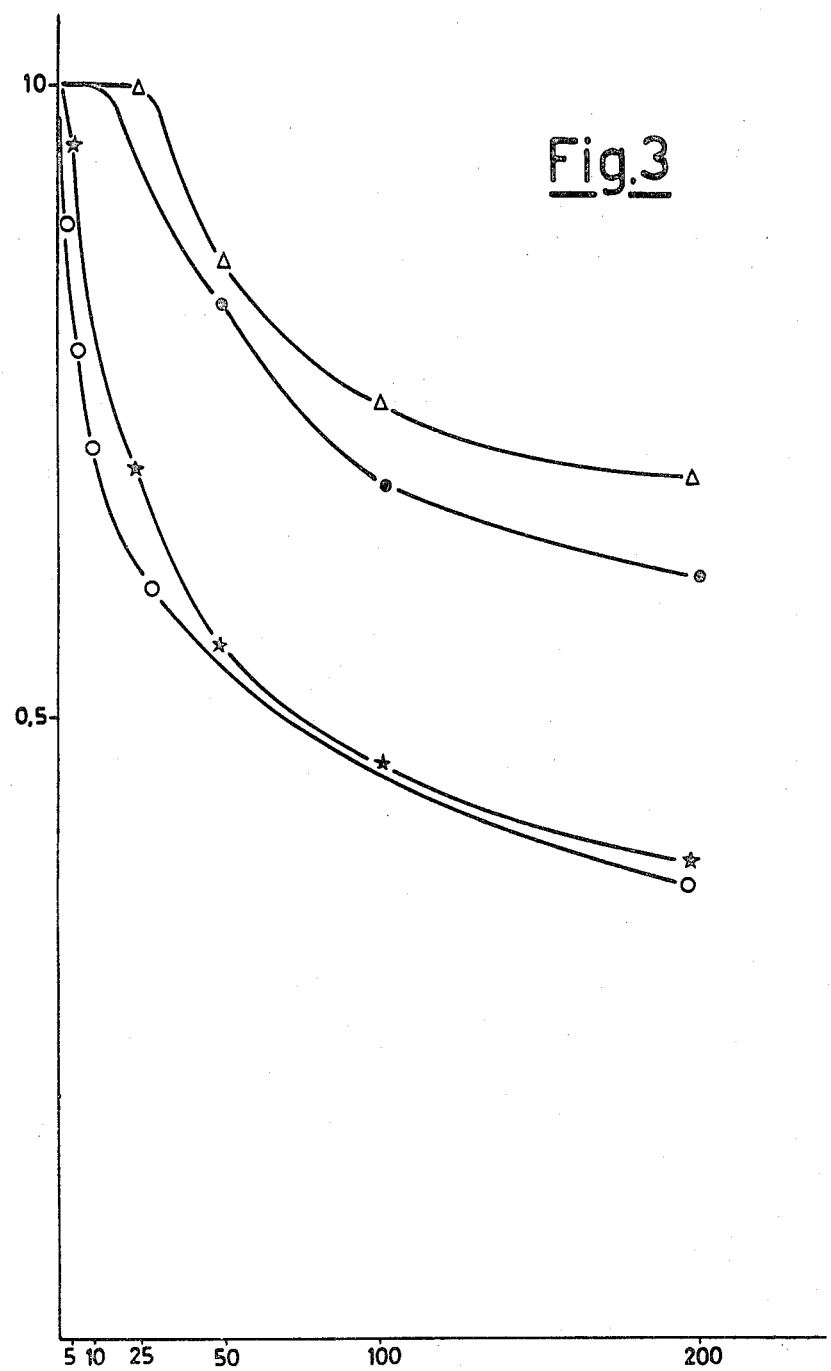
Figure 4:
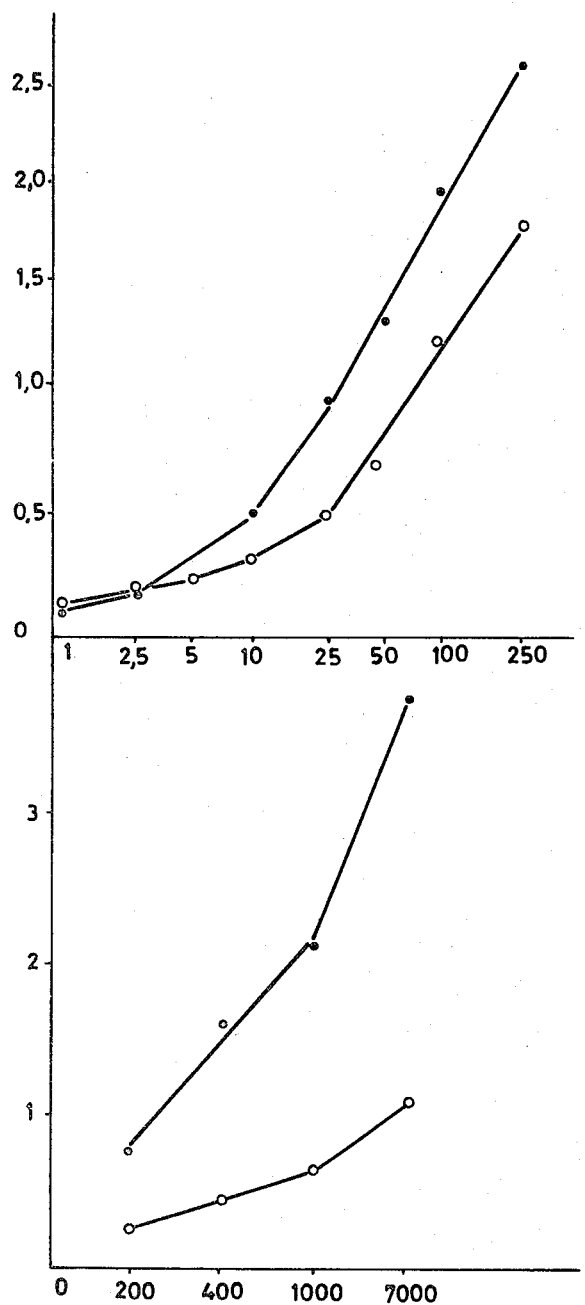

Variation of the standard curve as the surface area of the paper disc is varied (see explanation of FIG. 2, above) °23 sq.mm—*11.5 sq.mm—Δ5.7 sq.mm—Δ2.8 sq.mm

FIG. 4

Upper plot: The upper plot reports the standard initial curve (*) and that on the 32nd day as from the preparation (°) as obtained with the method "A".

Lower plot: The lower plot reports the initial standard curve (°) and that on the 32nd day as from the preparation (°) as obtained with the method "B".

The ordinates are the ratios (Rc−Ro)/Ro as explained above, and the abscissae are the concentrations of HCS in nanograms per milliliter.

We claim:
1. A method for quantitatively determining the presence of Human Chorionic Somatotropin (HCS) in a biological fluid comprising:

(a) forming a complex consisting essentially of an antagonist of HCS with the conjugation product of HCS and a tracer;
(b) introducing said complex into a sample of biological fluid suspected of containing HCS; and
(c) measuring the quantity of tracer which has been set free.

2. The method of claim 1 further comprising fixing the complex to a solid supporting member prior to introducing said complex into said sample.

3. The method of claim 1 wherein the solid supporting member is selected from the group consisting of cellulose in powder or paper form, cellulose having particular reactive groups as carboxymethyl or diethylaminoethyl in powder or paper form, polyvinyl chloride, polystyrene, nylon, polymethacrylate, polyamide, ureic resins, cellulose acetate, cellulose triacetate, cellulose nitrate, cellulose esters and ethers and derivatives thereof, and glass.

4. The method of claim 1 wherein the tracer is selected from the group consisting of radioisotopes, fluorescent substances, dyestuffs, enzymes, inhibitors of enzymatic and non-enzymatic reactions and complex-forming agents.

5. A composition adapted to quantitatively determine the presence of Human Chorionic Somatotropin (HCS) in a biological fluid which comprises a complex of an antagonist of HCS with the conjugation product of HCS and a tracer on a solid supporting member.

6. The composition of claim 5 wherein said tracer is selected from the group consisting of radioisotopes, fluorescent substances, dyestuffs, inhibitors of enzymatic and non-enzymatic reactions, and complex-forming agents.

7. A merchandising unit comprising containers of substances adapted to quantitatively determine the presence of HCS in a biological fluid formed by the composition of claim 5 and a set of reference standards of HCS having a known concentration.

8. The merchandising unit of claim 7 wherein the solid supporting member is selected from the group consisting of cellulose in powder or paper form, cellulose having particular reactive groups such as carboxymethyl or diethylaminoethyl in powder or paper form, polyvinyl chloride, polystyrene, nylon, polymethacrylate, polyamide, ureic resins, cellulose acetate, cellulose triacetate, cellulose nitrate, cellulose esters and ethers and derivatives thereof, and glass.

* * * * *